(12) United States Patent
Morville et al.

(10) Patent No.: US 7,450,240 B2
(45) Date of Patent: Nov. 11, 2008

(54) LASER DEVICE COUPLED TO A CAVITY BY OPTICAL FEEDBACK FOR DETECTING GAS TRACES

(75) Inventors: Jérôme Morville, Lyon (FR); Daniele Romanini, Grenoble (FR); Marc Chenevier, Saint Nazaire les Eymes (FR)

(73) Assignee: Universite Joseph Fourier, Grenoble (FR)

( * ) Notice: Subject to any disclaimer, the term of this patent is extended or adjusted under 35 U.S.C. 154(b) by 268 days.

(21) Appl. No.: 10/492,505

(22) PCT Filed: Oct. 9, 2002

(86) PCT No.: PCT/FR02/03438

§ 371 (c)(1),
(2), (4) Date: Oct. 18, 2004

(87) PCT Pub. No.: WO03/031949

PCT Pub. Date: Apr. 17, 2003

(65) Prior Publication Data

US 2005/0073687 A1    Apr. 7, 2005

(30) Foreign Application Priority Data

Oct. 10, 2001    (FR) .................................. 01 13052

(51) Int. Cl.
  *G01N 21/00*    (2006.01)
  *G01B 9/02*    (2006.01)
(52) U.S. Cl. .............................. 356/454; 372/9; 372/32; 372/92; 356/437

(58) Field of Classification Search ......... 356/436–440, 356/454, 422; 372/9, 32, 92
See application file for complete search history.

(56) References Cited

U.S. PATENT DOCUMENTS

| | | | | |
|---|---|---|---|---|
| 4,455,089 A | * | 6/1984 | Yeung et al. | 356/454 |
| 4,907,237 A | * | 3/1990 | Dahmani et al. | 372/32 |
| 5,432,610 A | * | 7/1995 | King et al. | 356/432 |
| 5,835,522 A | * | 11/1998 | King et al. | 372/97 |
| 5,903,358 A | * | 5/1999 | Zare et al. | 356/437 |
| 6,064,488 A | * | 5/2000 | Brand et al. | 356/440 |
| 6,084,682 A | * | 7/2000 | Zare et al. | 356/437 |
| 6,377,350 B1 | * | 4/2002 | Paldus et al. | 356/454 |

(Continued)

FOREIGN PATENT DOCUMENTS

WO    WO99/57542    11/1999

OTHER PUBLICATIONS

Morville, Kassi, Chenevier, and Romanini; Fast, low-noise, mode-by-mode, cavity-enhanced absorption spectroscopy by diode-laser self-locking; Appl. Phys. B 80, 1027-1038 (2005).*

*Primary Examiner*—Patrick J. Connolly
*Assistant Examiner*—Scott M. Richey
(74) *Attorney, Agent, or Firm*—Duane Morris LLP

(57) ABSTRACT

A device of detection of gas in trace amounts by a semiconductor laser coupled to a resonant optical cavity containing a chemical species to be analyzed. The device comprises a resonant optical cavity containing a chemical species to be analyzed; a semiconductor laser, coupled by optical feedback to the optical cavity and capable of being frequency-scanned; a means for adjusting the laser-cavity coupling rate; a means for finely adjusting the optical feedback phase; and a means for measuring the light transmitted by the cavity.

12 Claims, 7 Drawing Sheets

U.S. PATENT DOCUMENTS

| | | | |
|---|---|---|---|
| 6,466,322 B1 * | 10/2002 | Paldus et al. | 356/437 |
| 6,504,145 B1 * | 1/2003 | Romanini et al. | 250/227.23 |
| 6,611,546 B1 * | 8/2003 | Garnache et al. | 372/92 |
| 6,711,203 B1 * | 3/2004 | Garnache et al. | 372/92 |
| 7,012,696 B2 * | 3/2006 | Orr et al. | 356/454 |
| 2005/0134836 A1 * | 6/2005 | Paldus et al. | 356/73 |
| 2006/0056465 A1 * | 3/2006 | Xie et al. | 372/20 |
| 2006/0082778 A1 * | 4/2006 | Paldus et al. | 356/437 |
| 2006/0084180 A1 * | 4/2006 | Paldus et al. | 436/171 |
| 2006/0132766 A1 * | 6/2006 | Richman et al. | 356/318 |

\* cited by examiner

US 7,450,240 B2

LASER DEVICE COUPLED TO A CAVITY BY OPTICAL FEEDBACK FOR DETECTING GAS TRACES

RELATED APPLICATIONS

This application is a National Stage of International Application PCT/FR02/03438, filed on Oct. 9, 2002, which claims priority of French Application No. 01/13052 filed on Oct. 10, 2001.

BACKGROUND OF THE INVENTION

1. Field of the Invention

The present invention relates to the detection of gas in trace amounts. It more generally relates to a spectroscopy absorption measurement method in a resonant cavity.

2. Discussion of the Related Art

FIG. 1 illustrates the basic diagram of a method of spectroscopy absorption measurement in a resonant cavity. Light is emitted by a laser 1 in a resonant optical cavity 2 via an optical coupling system 3. The light coming out of the resonant cavity is received by a photodetector 4 and is sent to an analyzer 5. If the laser frequency varies, there will be a maximum of the signal received by the photodetector for each cavity mode. If the cavity contains a chemical species exhibiting an absorption line at the wavelengths of the injected photons, the transmission will be reduced according to the absorption. Based on the transmission spectrum, the absorption spectrum is obtained in the same way as for a conventional absorption spectrum. But, then, the absorption signal is multiplied by the cavity thinness and it should normally be possible to perform absorption measurements with a very high sensitivity. A transmission curve showing the transmitted intensity versus frequency expressed as a ratio of C/2L, where C is the speed of light and L is the length of the resonant cavity, is illustrated in FIG. 2A, and the absorption of the chemical species contained in the cavity versus frequency illustrated in FIG. 2B can be deduced from this curve.

Unfortunately, in practice, such methods of direct measurement by spectroscopy in a resonant cavity are impossible or very complex to implement. Indeed, a sufficient power has to be injected into the cavity, this power must be constant or follow a known variation, and the detected signal must not be too noisy.

To avoid these disadvantages, methods of detection by optical power decrease in a resonant cavity, currently designated as CRDS, for cavity ring-down spectroscopy have been used. According to this method, the laser beam is sent into the cavity, after which the photon injection is abruptly stopped. The photons then remain trapped in the cavity and their intensity decreases exponentially along time. If the cavity is empty, or for a wavelength that does not correspond to an absorption line of a gas contained in the cavity, this decrease will exhibit a given time constant essentially determined by the mirror losses at the considered wavelength. If the cavity contains a chemical species exhibiting an absorption line at the wavelength of the injected photons, this time constant will be reduced. An advantage of this method is that it gets rid of the noise due to fluctuations of the intensity injected into the cavity.

To inject a sufficient quantity of light into the resonant cavity, a method of CRDS type in which the frequency of a continuous semiconductor laser is controlled by an optical feedback from the cavity has been provided. Such a method is described in PCT patent application WO99/57542. This method provides satisfactory results, but the absorption curve determination time is relatively long since, for each measurement, a single point of the absorption curve is calculated.

SUMMARY OF THE INVENTION

Thus, an object of the present invention is to provide a method for measuring traces of a chemical species by the direct use of a resonant cavity spectroscopy method in which the photon injection into the resonant cavity from a continuous-wave laser is optimized.

To achieve this object, the present invention provides a device for detecting gas in trace amounts comprising a resonant optical cavity containing a chemical species to be analyzed; a laser sensitive to an optical feedback, coupled by optical feedback to the optical cavity and capable of being frequency-scanned; a means for adjusting the laser-cavity coupling rate; a means for finely adjusting the optical feedback phase; and a means for measuring the light transmitted by the cavity.

According to an embodiment of the present invention, the device comprises a means for roughly adjusting the distance from the laser to the cavity.

According to an embodiment of the present invention, the means for finely adjusting the phase of the optical feedback is a means for setting the laser-cavity optical distance.

According to an embodiment of the present invention, the fine adjustment means is a reflection mirror assembled on a piezo-electric ceramics arranged in the optical path from the laser to the cavity.

According to an embodiment of the present invention, at the means for adjusting the laser-cavity coupling rate is an optical attenuator attenuating the light sent back by the cavity to the laser, such as a Faraday cell.

According to an embodiment of the present invention, the laser is a laser diode.

According to an embodiment of the present invention, the cavity is of V-shaped type, comprising a first mirror oblique with respect to the laser incidence direction, a second mirror orthogonal to the laser incidence direction, and a third mirror forming a cavity with the first two mirrors.

According to an embodiment of the present invention, the cavity is a conventional two-mirror cavity.

According to an embodiment of the present invention, the ratio between the laser-cavity distance and the length of one or several arms of the cavity is equal to an integer, to the inverse of an integer, or to a ratio of integers.

The present invention also aims at a method for using the above device consisting of varying the laser-cavity optical path by a value on the order of the laser wavelength.

The foregoing objects, features, and advantages of the present invention will be discussed in detail in the following non-limiting description of specific embodiments in connection with the accompanying drawings.

DETAILED DESCRIPTION

Before describing the present invention, the applicant insists on recalling that, in the field of optical spectroscopy, terms such as thin line, monomode system, etc. often have different meanings according to authors. The vocabulary which will be used herein will thus be specified hereafter in relation with FIGS. 3A to 3C.

Figure 3A:
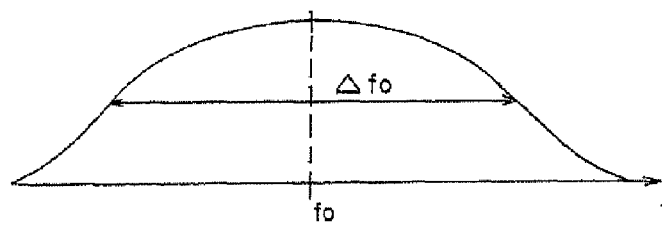
FIGS. 3A to 3C show curves according to frequency, respectively for an absorption line, or a laser line and for longitudinal modes of a cavity.

FIG. 3A shows the intensity of an absorption line of a gas species according to frequency. The line has a central frequency f0 and a width $\Delta f0$. As an example, the absorption line at 1651 nm of methane has an absorption line width $\Delta f0$=4.4 GHz (which corresponds to a 0.04-nm wavelength range).

Figure 3B:
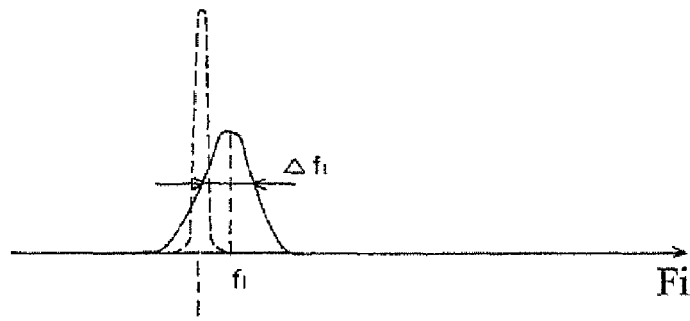

A continuous-wave laser such as a laser diode or another semiconductor laser with a settable frequency will emit a line f1 of width $\Delta f1$ such as shown in FIG. 3B. Generally, $\Delta f1$ will be much smaller than width $\Delta f0$ of the absorption line, and this case will always be considered herein.

Figure 3C:
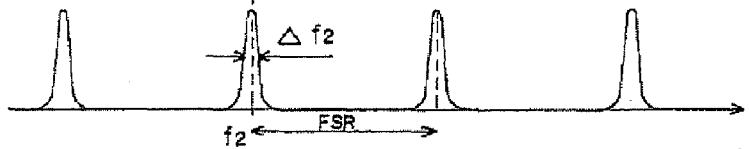

Further, as illustrated in FIG. 3C, a resonant optical cavity of given length may resound on one or the other of several frequencies or longitudinal modes spaced apart by a distance FSR or free spectral range. To simplify the discussion, the frequency of a cavity mode will be called f2, noting that it should be spoken of a frequency f2+kFSR where k is a positive, negative, or zero integer. For each of the longitudinal modes, the possible resonance width $\Delta f2$ is very small, that is, small as compared to width $\Delta f1$ of the laser line, which is itself very small as compared to width $\Delta f0$ of the absorption line. The case, frequent in practice, where $\Delta f1$ is smaller than distance FSR between cavity modes will be considered. For example, FSR may be equal to 300 MHz (approximately 10 times less than the width of the absorption line to be studied).

As shown in FIG. 3B, the laser line power is distributed on a time average over the frequencies belonging to width $\Delta f1$ and only the hazardous correspondence of the frequencies within the width of the mode of cavity $\Delta f2$ will enable injection into the cavity. It can thus be seen that the quantity of photons injected into the cavity is small as compared to the total intensity of the laser line. Further, this quantity will fluctuate due to the fluctuations of the laser frequency and the measurements will be affected by a significant noise. According to the present invention, the resonant cavity is used as the source of a positive optical feedback at the frequencies of the resonance modes towards the laser, which is chosen of a type strongly reacting to an optical feedback.

It should be reminded that the resonant cavity, to be efficient from the point of view of the absorption detection, must exhibit highly reflective mirrors, for example, mirrors having a reflection coefficient close to 99.998, which corresponds to a fineness on the order of 150,000. Thus, when the laser sends light onto input mirror 2-1 of the resonant cavity, this light is mostly sent back onto the laser. This is likely to disturb the laser. This is why in conventional assemblies, an optical isolator is used between the laser and the cavity. In the context of the present invention, an assembly capable of selectively sending back onto the laser a waveband having a width corresponding to the width of a cavity mode for a resonance frequency of the cavity is used. If the laser emits power around frequency f1 (FIG. 3B) and the laser line contains power at a frequency f2, the cavity starts resonating and only the waves corresponding to this resonance frequency are sent back onto the laser. If the laser is sensitive to an optical feedback, which is the case, for example, for semiconductor lasers, the laser line will become thinner and will intensify on the reflected bandwidth. Thus, the laser, instead of sending a line of width $\Delta f1$ centered on frequency f1, will send an intense line having a width smaller than $\Delta f2$ centered on frequency f2 of a cavity mode, as shown in dotted lines in FIG. 3B. Thus, the laser will only send into the cavity photons at the wanted frequency (a resonance frequency of the cavity) and the injection will reach its optimum. It can be said that the laser is controlled by a cavity mode.

Figure 4A:
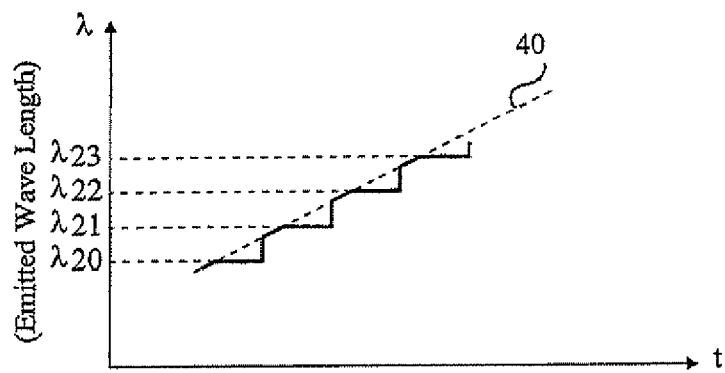
FIGS. 4A and 4B show curves characterizing the frequency lock-in between a laser and a cavity in the presence of an optical feedback.
Figure 4B:
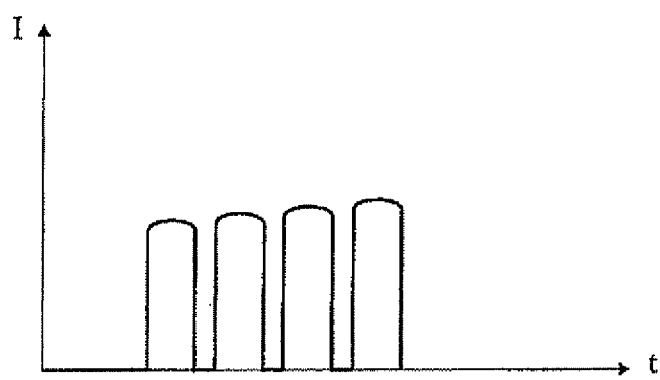

Considering a laser diode, when a current ramp is applied, as shown by curve 40 in dotted lines of FIG. 4A, the emitted wavelength $\lambda$ tends to progressively increase. As indicated, due to the coupling with the cavity, for each of the natural frequencies or frequencies of the longitudinal modes of the cavity, $f2_0$, $f2_1$, $f2_2$, $f2_3$ ..., the laser frequency will tend to lock-in on the considered frequency. Thus, the cavity transmission is substantially such as shown in FIG. 4B, that is, the cavity transmits for each lock-in frequency $f2_0$, $f2_1$, $f2_2$, $f2_3$ ...

The foregoing describes the ideal case where the optical feedback is optimized for all the cavity modes covered by the laser scanning. In practice, this situation is not obtained: the intensity differs from one mode to the other and instabilities are observed.

The object of the present invention is to provide arrangements to the optical assembly providing satisfactory measurements.

According to a first aspect of the present invention, it is provided to improve the laser-cavity coupling. Indeed, in many cases, the action of an optical feedback on a laser makes the lock-in thereof on a cavity mode extremely strong. Accordingly, when the laser current is modified to normally have it perform a frequency scanning, instead of remaining blocked by optical feedback on a free spectral range fraction only, as shown in FIG. 4A, the laser tends to remain locked for a longer time, currently over an interval greater than a free spectral range, or even possibly over two or more free spectral ranges and this, irregularly from one mode to another or from one scanning to another. The obtained measurement then is no longer significant since the sampling of the absorption curve is no longer regular. To overcome this disadvantage, the present invention provides placing in the path between the laser and the cavity a settable attenuator, preferably active only to attenuate the wave returning from the cavity to the laser or more generally the laser-cavity coupling rate. A Faraday attenuator may for example be selected. This attenuator is set so that the coupling rate is capable of providing a lock-in range slightly smaller than the interval between the cavity modes or than an integral multiple of this interval.

According to a second aspect of the present invention, the present inventors have also shown that another significant parameter is a satisfactory tuning between the phase of the wave emitted by the laser and the phase of the wave sent back by the cavity.

Figure 5:
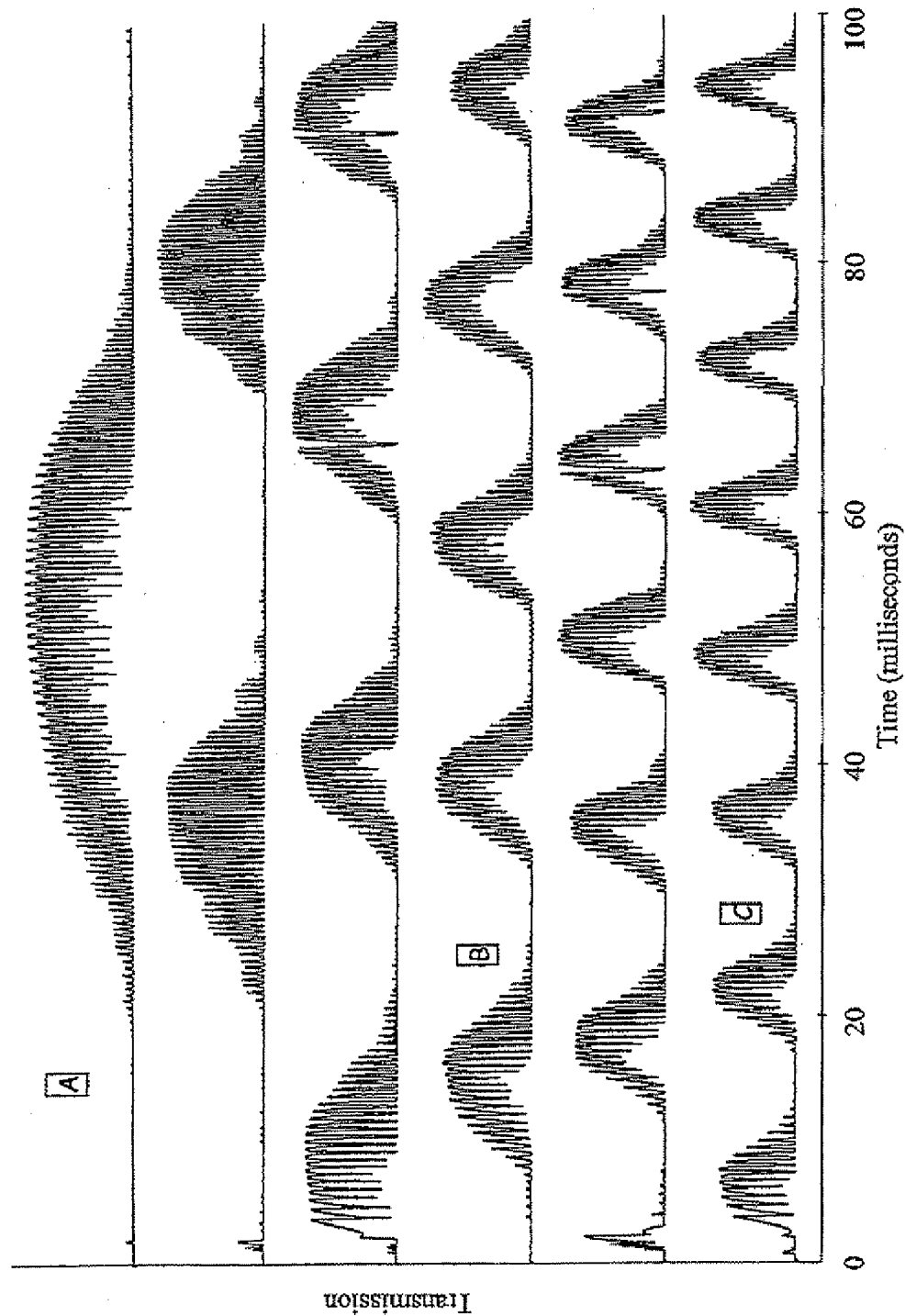
FIG. 5 shows the shape of the cavity transmission curve obtained for various adjustments of the cavity length with respect to the laser-cavity distance.

FIG. 5 shows the shape of the transmission obtained at the output of a cavity when the laser frequency is scanned through several modes of this cavity with an optical feedback as described previously. The laser-cavity phase condition can be modified by an adjustment of distance $L_b$ between the laser and the cavity. When this distance is of the same order of magnitude as length L of an arm of the cavity (assuming a single cavity or a cavity with two equal arms), a substantially flat curve is obtained. When this distance becomes equal to 95% of the cavity length, a transmission curve such as that shown in A in FIG. 5 is obtained. For 85%, a curve such as that shown in B is obtained, and for 70%, a curve such as that shown in C is obtained. The other curves of FIG. 5 are intermediary curves.

Thus, according to an embodiment of the present invention, a case where the laser-cavity distance is equal to the length of the cavity or to an integral multiple of this length is considered to obtain a substantially flat (or slightly increasing) transmission figure such that all the cavity modes scanned by the laser are also excited at the transmission maximum. It is further possible for judiciously chosen laser-cavity distances to strictly excite one mode out of two, or out of three, etc., each of these modes being also excited at the transmission maximum and a flat transmission figure is obtained again; that is, the laser-cavity distance may be an integral sub-multiple of the cavity length (more possibly an integral number of times the cavity length). As indicated hereafter, another configuration may be used provided to modulate the laser-cavity distance.

Figure 6:
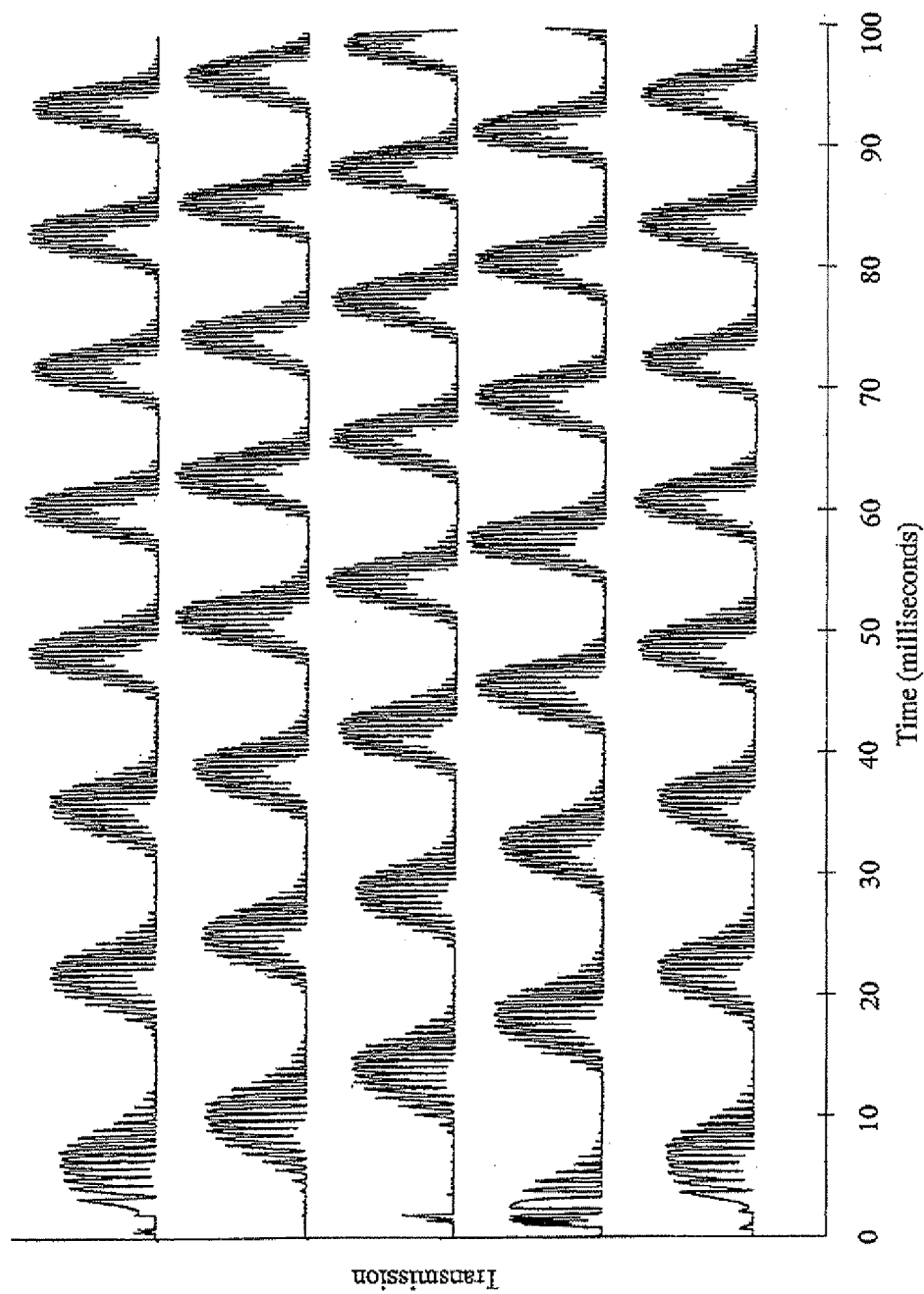
FIG. 6 shows, for a given laser-cavity distance, the influence of a small variation (on the order of $\lambda/2$) of this distance.

FIG. 6 shows, at its top, a curve similar to that of FIG. 5C. The cavity transmission curve comprises groups of modes for which the intensity is relatively strong, separated by groups of modes of very small intensity.

On the other hand, if the laser-cavity distance is varied by on the order of half a wavelength, it is progressively passed from the curve shown at the upper line of FIG. 6 to the curve shown at the lower line of FIG. 6. Thus, in average, if several measurements are performed and the laser-cavity distance is modulated on a range greater than $\lambda/2$, there will be in average a flat curve and the factors linked to the cavity absorption can thus be determined.

Figure 7:
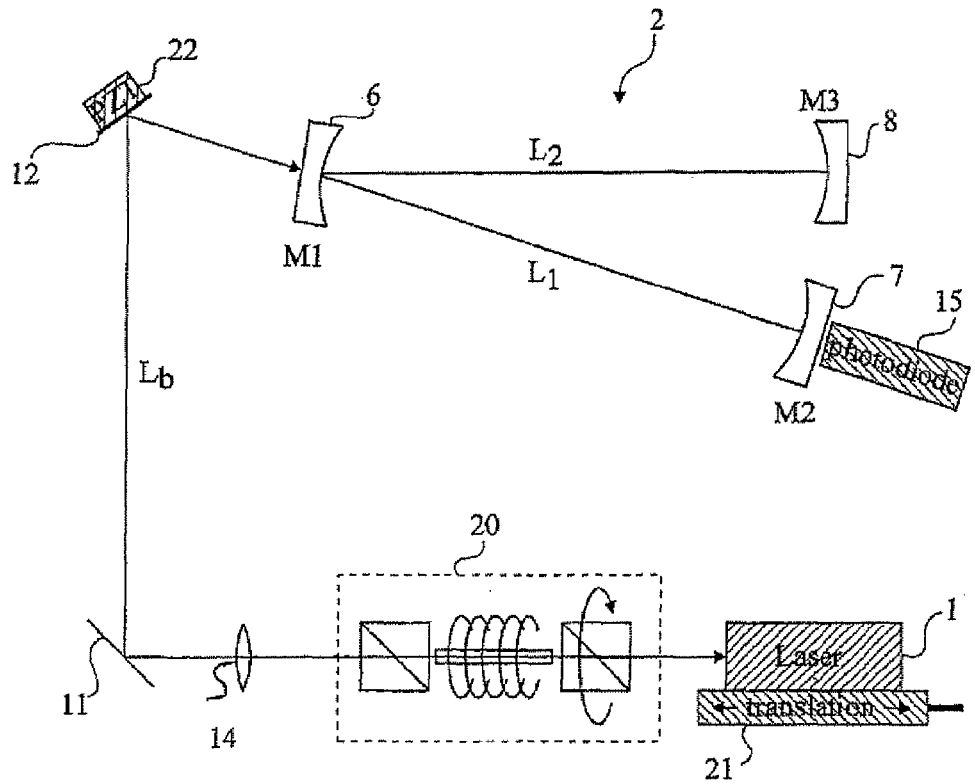
FIG. 7 shows a specific embodiment of a device according to the present invention.
Figure 8:
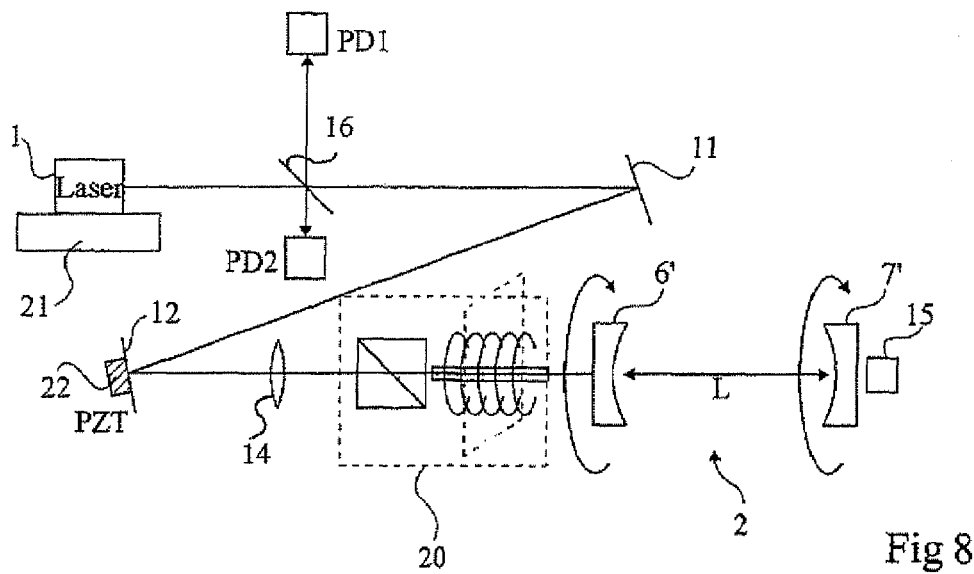
FIG. 8 shows another specific embodiment of a device according to the present invention.

Examples of devices implementing the present invention are illustrated in FIGS. 7 and 8.

Figure 1:
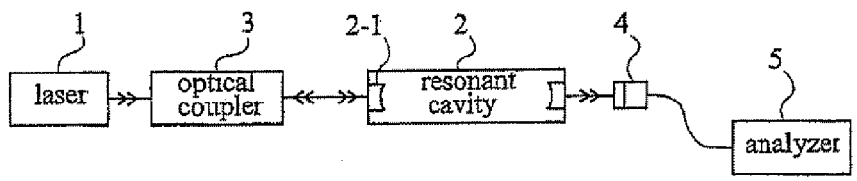
FIG. 1 shows the general diagram of a device implementing a method of spectroscopy absorption measurement in a resonant cavity.
Figure 2A:
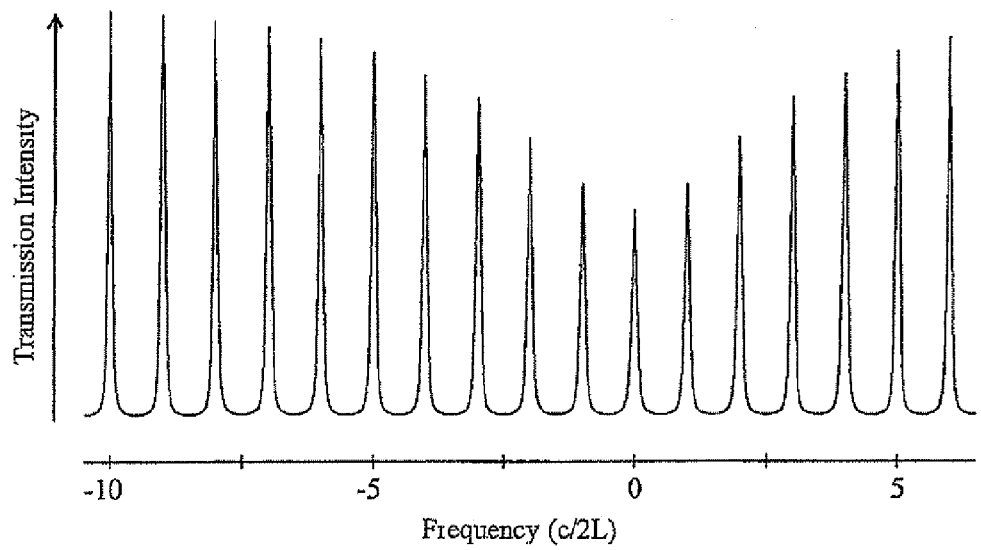
FIGS. 2A and 2B respectively show the transmission of a resonant cavity containing a chemical species excited mode by mode at constant intensity and the absorption curve of the species.
Figure 2B:
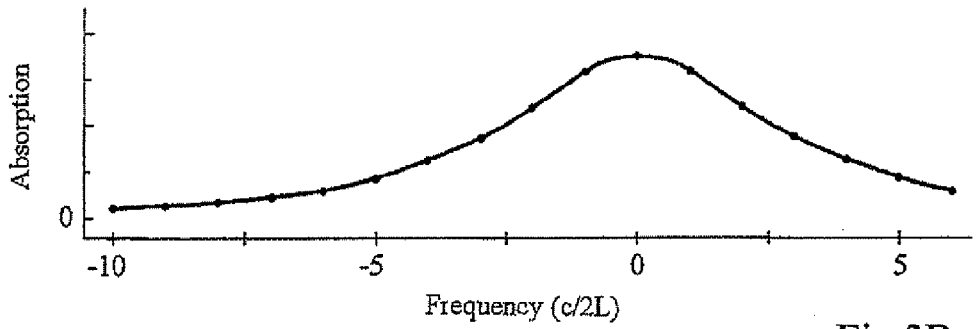

In FIG. 7, the laser is designated with reference 1. Cavity 2 is a V-shaped cavity comprising an input mirror 6 and mirrors 7 and 8 arranged substantially as shown to form a resonant cavity. The direct beam sent by the laser is reflected by mirrors 11 and 12 to the rear surface of mirror 6 and to second mirror 7. The light reflected by mirror 7 is reflected by the front surface of mirror 6 to mirror 8. When the cavity is not tuned, the general beam sent by the laser and reaching the rear surface of the mirror is not directed in return towards the laser. The direct beam arriving onto mirror 7 is sent back to mirror 6. However, its intensity at the output of mirror 6 is extremely small since it undergoes the double transmission attenuation of mirror 6 and can be considered as negligible as long as cavity 2 is not tuned. The intensity sent back becomes significant only when the resonance wavelength of the cavity (f2 in FIG. 3C) is sent by the laser. Then, the feedback and line thinning phenomenon occurs. A maximum injection then occurs in the cavity. A photodetector 15, arranged for example behind one of mirrors 7 or 8, enables studying the transmission curve linked to the presence or to the absence of an absorption line of a species searched for in the cavity, as illustrated in FIG. 2A.

According to the present invention, as discussed previously, a Faraday isolator 20 is introduced between the laser and the cavity. With a laser diode, an adjustable Faraday isolator of low quality and cost that can exhibit an attenuation rate ranging between $\frac{1}{10}$ and $\frac{1}{1000}$ may be used. The arrow symbolizes the rotation of the optical polarization induced by the adjustable Faraday isolator. The laser is assembled on a device 21 enabling its setting in translation and one of the reflection mirrors, for example, mirror 12, is assembled on a piezo-electric ceramic 22 to enable control and especially modulation of the optical path over a range on the order of the laser wavelength. Conversely to what is shown in the drawing, distance $L_b$ between the rear surface of mirror M1 and the laser output is of the same order of magnitude as length L1 of a cavity arm (assuming that the two arms have the same length). Further, various known conventional means of prior art devices may be used. For example, separators 16 may be used to deflect portions of the laser beam towards other photodetectors or towards a reference cell that can be associated with a detector to enable initial setting of the laser.

FIG. 8 shows as an example an alternative embodiment of the present invention in which same elements as in FIG. 7 are designated with same reference numerals. In this embodiment, resonant cavity 2 is a conventional cavity formed of two opposite mirrors 6' and 7' and a polarization isolator is arranged between the laser and the cavity to prevent the returning to the laser of a direct reflection on the rear surface of the input mirror and to transmit to the laser a radiation having undergone a resonance in the cavity, the polarization of which has been modified during the multiple comes and goes. The arrows symbolize the rotation of the optical polarization induced by the isolator.

Other elements such as a lens 14 will also be preferably provided in the two assemblies FIGS. 7 and 8 to adjust the transverse modes of the laser and of the cavity.

Figure 9:
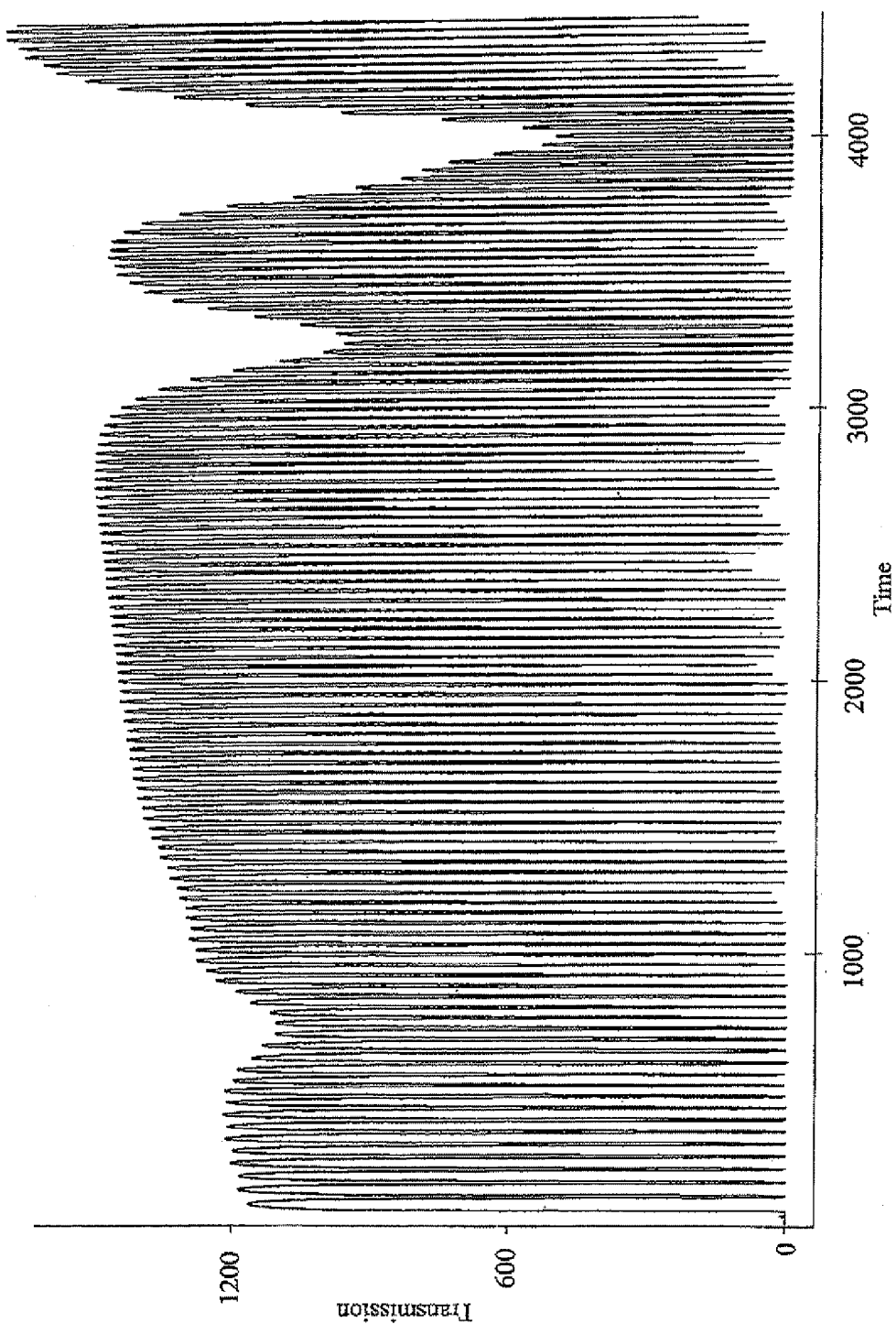
FIG. 9 shows an example of a spectrum obtained according to the present invention for a tuned laser-cavity distance.

FIG. 9 shows an example of the transmission of a cavity according to the present invention containing water vapor for an optimal setting of the laser-cavity distance. It should be noted that the intensity of the modes is substantially constant (in fact, regularly increasing) except at the locations where water vapor absorption lines appear.

Influence of the Transverse Modes of the Cavity

In the foregoing description, and more specifically in FIG. 3C, the cavity has been shown as exhibiting resonance modes at frequencies f2 separated from one another by an interval equal to the free spectral range FSR of the cavity. This was a simplification. Indeed, a cavity is likely to resonate on several transverse electromagnetic modes (TEM), generally designated as $TEM_{ij}$.

To avoid the influence of these lateral modes, a cavity set to operate in a mode close to a degenerated mode, the secondary transverse modes being all gathered on one side of a corresponding main transverse mode, the laser performing a scanning in the direction towards the side opposite to that where the secondary lateral modes are located, may be chosen as explained in PCT patent application WO99/57542.

Of course, the present invention is likely to have various alterations, modifications, and improvements which will readily occur to those skilled in the art. In particular, various types of cavities and various analysis systems, as well as various systems for controlling the intensity and the feedback phase, may be used. Cavities with two confocal mirrors or cavities with more than three mirrors may for example be used. The relation between the laser-cavity distance and the length of the cavity arm(s) is chosen accordingly. Temperature regulation systems may also be provided to especially stabilize the cavity and the Faraday cell.

The invention claimed is:

1. A device for detecting gas in trace amounts, comprising:
   a resonant optical cavity containing a chemical species to be analyzed;
   an optical feedback sensitive laser coupled by optical feedback to the resonant optical cavity and capable of being frequency-scanned;
   a means for adjusting a laser-cavity coupling rate to provide improved laser-cavity coupling;
   a means for finely adjusting the phase of the optical feedback; and
   a means for measuring the light transmitted by the cavity.

2. The device of claim 1, wherein the device comprises a means for roughly adjusting the distance from the optical feedback sensitive laser to the resonant optical cavity.

3. The device of claim 1, wherein the means for finely adjusting the phase of the optical feedback is a means for setting a laser-cavity optical distance.

4. The device of claim 3, wherein the means for finely adjusting the phase of the optical feedback is a mirror disposed on a piezo-electric ceramic arranged in the optical path from the optical feedback sensitive laser to the resonant optical cavity.

5. The device of claim 1, wherein the means for adjusting the laser-cavity coupling rate is an optical attenuator attenuating the light sent back by the resonant optical cavity to the optical feedback sensitive laser.

6. The device of claim 1, wherein the optical feedback sensitive laser is a laser diode.

7. The device of claim 1, wherein the resonant optical cavity is of a V-shaped type, comprising a first mirror oblique with respect to a laser incidence direction, a second mirror orthogonal to the laser incidence direction, and a third mirror forming a cavity with the first and second mirrors.

8. The device of claim 1, wherein the resonant optical cavity is a conventional two-mirror cavity.

9. A method for using the device of claim 1, comprising the step of adjusting the ratio between a laser-cavity distance and a length of one or several arms of the resonant optical cavity to an integer.

10. A method for using the device of claim 1, comprising the step of varying a laser-cavity optical path by a value on the order of the laser wavelength.

11. A device for detecting gas in trace amounts, comprising:
    a resonant optical cavity containing a chemical species to be analyzed;
    an optical feedback sensitive laser coupled by optical feedback to the resonant optical cavity and capable of being frequency-scanned;
    an optical attenuator for adjusting the laser-cavity coupling rate to provide improved laser-cavity coupling;
    a mirror disposed on a piezo-electric ceramic for finely adjusting the phase of the optical feedback; and
    a photodetector for measuring the light transmitted by the cavity.

12. A device for detecting gas in trace amounts, the device comprising:
    a resonant optical cavity containing a chemical species to be analyzed, the resonant oDtical cavity having several arms;
    an optical feedback sensitive laser disposed at a distance from the resonant optical cavity and coupled by optical feedback to the resonant optical cavity and capable of being frequency- scanned;
    a means for adjusting the laser-cavity coupling rate;
    a means for finely adjusting the phase of the optical feedback; and
    a means for measuring the light transmitted by the resonant optical cavity,
    wherein the ratio between the distance and a length of one or the several arms of the resonant optical cavity is adjusted to be an integer.

* * * * *